(12) United States Patent
Lavery et al.

(10) Patent No.: US 10,510,348 B1
(45) Date of Patent: Dec. 17, 2019

(54) SMART MEDICAL ROOM OPTIMIZATION OF SPEECH RECOGNITION SYSTEMS

(71) Applicant: INTERNATIONAL BUSINESS MACHINES CORPORATION, Armonk, NY (US)

(72) Inventors: Andrew J. Lavery, Austin, TX (US); Kenney Ng, Arlington, MA (US); Michael A. Picheny, White Plains, NY (US); Paul C. Tang, Los Altos, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/145,572

(22) Filed: Sep. 28, 2018

(51) Int. Cl.
*G10L 21/00* (2013.01)
*G10L 15/26* (2006.01)
*G10L 15/22* (2006.01)
*G16H 80/00* (2018.01)
*G16H 10/60* (2018.01)

(52) U.S. Cl.
CPC ............ *G10L 15/265* (2013.01); *G10L 15/22* (2013.01); *G16H 10/60* (2018.01); *G16H 80/00* (2018.01); *G10L 2015/228* (2013.01)

(58) Field of Classification Search
CPC .... A61N 1/37247; G16H 30/20; G10L 15/22; G10L 15/063; G10L 15/30; G10L 15/16; G10L 15/26; G10L 2015/0635; G10L 2015/225; G10L 15/32; G10L 15/00; G10L 15/06; G10L 17/00; G10L 17/005; G10L 17/04; G10L 17/22; G10L 25/48

USPC ........................ 704/1-10, 230-257, 270-277
See application file for complete search history.

(56) References Cited

U.S. PATENT DOCUMENTS

| 7,805,299 B2 | 9/2010 | Coifman |
| 9,348,813 B2 | 5/2016 | Mankovich et al. |
| 2001/0032085 A1* | 10/2001 | Goedeke ............ A61N 1/37247 704/275 |
| 2004/0102971 A1 | 5/2004 | Lipscher et al. |

(Continued)

OTHER PUBLICATIONS

Mell et al., "The NIST Definition of Cloud Computing," National Institute of Standards and Technology, Sep. 2011, p. 1-3, Special Publication 800-145.

(Continued)

*Primary Examiner* — Huyen X Vo
(74) *Attorney, Agent, or Firm* — Nicole A. Spence

(57) ABSTRACT

A method, computer system, and a computer program product for optimizing speech recognition in a smart medical room. The present invention may include receiving a piece of verbal data associated with a medical encounter from one or more audio recording devices. The present invention may also include accessing a plurality of signals from a plurality of biometric sensors associated with a plurality of medical equipment associated with the smart medical room based on the received piece of verbal data associated with the medical encounter. The present invention may further include selecting, from a database, one or more speech domain models based on the accessed plurality of signals from the plurality of biometric sensors associated with the plurality of medical equipment, wherein the one or more speech domain models are utilized to optimize a transcription of speech during the medical encounter in the smart medical room.

20 Claims, 5 Drawing Sheets

(56) References Cited

U.S. PATENT DOCUMENTS

| | | |
|---|---|---|
| 2006/0036430 A1 | 2/2006 | Hu |
| 2008/0040099 A1 | 2/2008 | Wu et al. |
| 2008/0091633 A1 | 4/2008 | Rappaport et al. |
| 2013/0238330 A1* | 9/2013 | Casella dos Santos ............ G10L 15/183 704/235 |
| 2013/0317753 A1* | 11/2013 | Kamen ............... G06F 19/3418 702/19 |
| 2014/0019128 A1 | 1/2014 | Riskin et al. |
| 2014/0379378 A1 | 12/2014 | Cohen-Solal et al. |
| 2019/0080796 A1* | 3/2019 | Greiner .................. G16H 30/20 |

OTHER PUBLICATIONS

M*Modal, "Closing the Loop in Clinical Documentation," M*Modal Closed-Loop Clinical Documentation Solutions, p. 1-3, MModal IP LLC, https://mmodal.com/, Accessed on Sep. 27, 2018.

Nuance, "Dragon Medical Speech Solutions for Clinicians," Nuance—Best Medical Dictation and Clinical Documentation Software, p. 1-6, Nuance Communications Inc., https://www.nuance.com/healthcare/physician-and-clinical-speech/dragon-medical.html, Accessed on Sep. 27, 2018.

\* cited by examiner

SMART MEDICAL ROOM OPTIMIZATION OF SPEECH RECOGNITION SYSTEMS

BACKGROUND

The present invention relates generally to the field of computing, and more particularly to healthcare.

An important part of caring and treating patients is understanding and transcribing the audio conversation between a clinician and a patient. The possibilities of the conversation are vast and the resulting transcript should accurately include the entire conversation for the clinician to review at later time for diagnosing and treating the patient. Currently, many clinicians have opted to hire a person to act as a scribe and manually record and transcribe the conversation, which is an expensive solution to transcribing a conversation.

SUMMARY

Embodiments of the present invention disclose a method, computer system, and a computer program product for optimizing speech recognition in a smart medical room. The present invention may include receiving a piece of verbal data associated with a medical encounter from one or more audio recording devices. The present invention may also include accessing a plurality of signals from a plurality of biometric sensors associated with a plurality of medical equipment associated with the smart medical room based on the received piece of verbal data associated with the medical encounter. The present invention may further include selecting, from a database, one or more speech domain models based on the accessed plurality of signals from the plurality of biometric sensors associated with the plurality of medical equipment, wherein the one or more speech domain models are utilized to optimize a transcription of speech during the medical encounter in the smart medical room.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
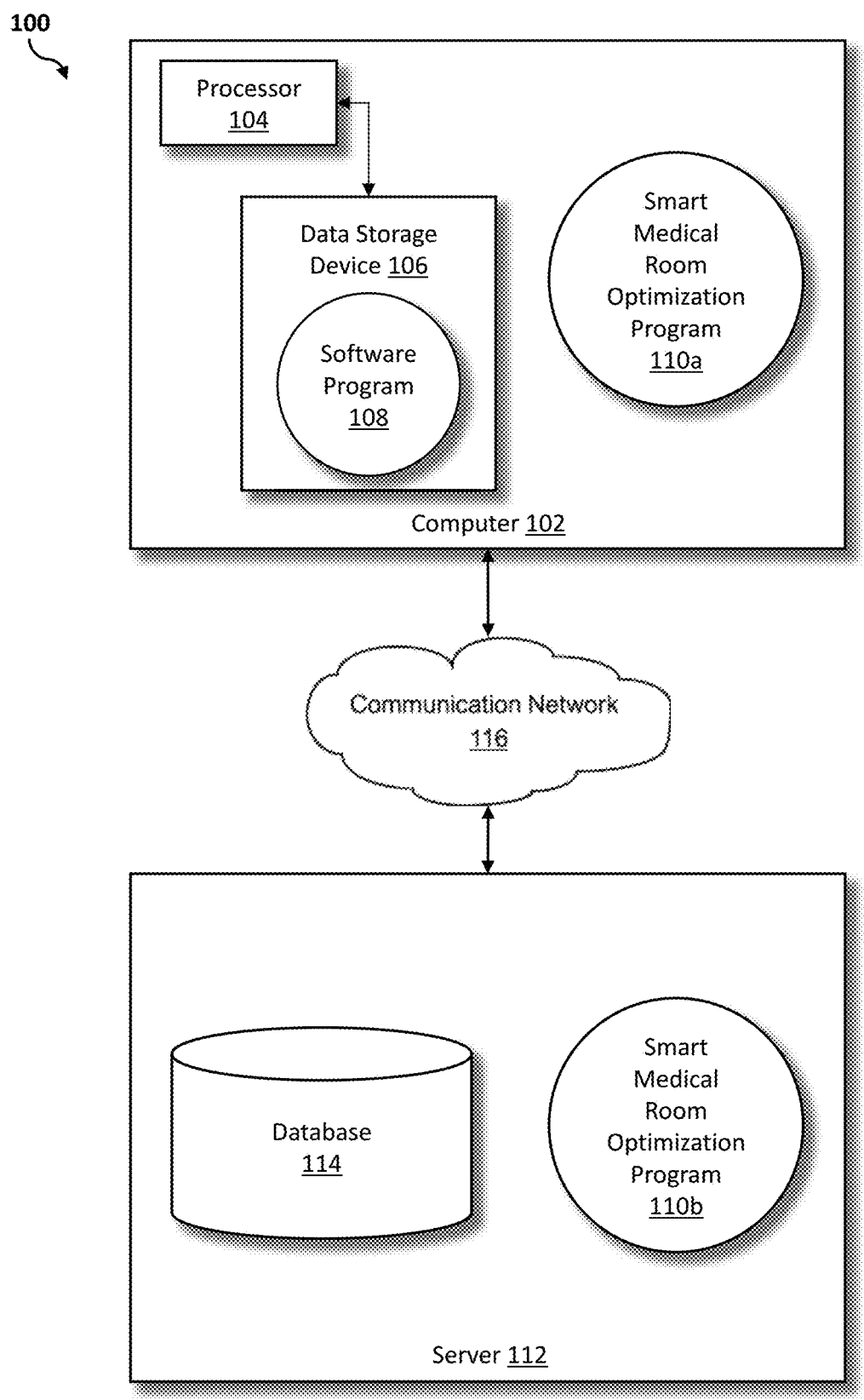
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language, Python programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for optimizing speech recognition in a smart medical room. As such, the present embodiment has the capacity to improve the technical field of healthcare by intelligently selecting at least one domain model to focus the conversation between the clinician and the patient in a smart medical room. More specifically, the smart medical room optimization program may utilize continuous monitoring of the conversation between the clinician and the patient and continuous access to the equipment status in the smart medical room to intelligently select the appropriate domain model(s) for each stage of the conversation from a database of trained domain models.

As previously described, an important part of caring and treating patients is understanding and transcribing the audio conversation between a clinician and a patient. The possibilities of the conversation are vast and the resulting transcript should accurately include the entire conversation for the clinician to review at later time for diagnosing and treating the patient. Currently, many clinicians have opted to hire a person to act as a scribe and manually record and transcribe the conversation, which is an expensive solution to transcribing a conversation.

Speech recognition systems may be utilized to provide transcripts of these conversations. However, speech recognition systems have difficulty honing in on the exact conversation. Solving this problem is important as digital scribes for the healthcare industry are becoming more important and valuable. There have been additional attempts to use speech to text services; however, these solutions are still not currently accurate enough for conversational medical transcription.

Therefore, it may be advantageous to, among other things, use the knowledge of dynamic device and equipment status in a smart medical room as input in a speech recognition system to focus the speech recognition domain model and improve accuracy over the course of a medical examination or medical encounter.

According to at least one embodiment, the smart medical room optimization program may be utilized to intelligently find the correct domain model based on continuous monitoring of the device and equipment status in a smart medical room.

According to at least one embodiment, the smart medical room optimization program may be integrated into another program (e.g., Speech to Text system by IBM® (IBM and all IBM-based trademarks and logos are trademarks or registered trademarks of International Business Machines Corporation and/or its affiliates)) that trains customized domain models and switches the trained domain model to better match the conversation. The Speech to Text system may allow for customized domain models to be trained that are primed to more accurately recognize certain types of conversations (e.g., ordering food at a particular restaurant, discussion of car rental policies/questions/orders, medical interview of past medical history of a patient).

According to at least one embodiment, the smart medical room optimization program may be equipped with devices that provide feedback on their status. For example, an exam chair/bed (i.e., examination furniture) may provide status of whether patient is in the chair or not, whether the exam chair is reclined back for patient exam, or whether the exam chair is supporting the patient who is sitting up. A stethoscope may provide status of whether a clinician is utilizing the stethoscope on the patient, or whether the stethoscope is resting around the clinician's neck, and potentially even sounds from the stethoscope to have backend software analyze the sounds in addition to the clinician analyzing the sounds. Other medical devices, for example, may be instrumented in a similar way to provide feedback of their use, such as blood pressure cuff, weight scale, otoscope (i.e., ear exam device), syringe, drug infusion device, ophthalmology equipment for examining or treating eyes, and medical imaging equipment.

According to at least one embodiment, the smart medical room optimization program may be equipped with active badge technology to identify the specialists in the medical room. As such, the smart medical room optimization program may be aware of the role and specialty (e.g., an internal medicine generalist, a cardiologist, a nurse, a radiologist) of clinicians present in the room.

According to at least one embodiment, the smart medical room optimization program may include a camera or sensors in the room to detect the proximity of the clinician to the patient. Therefore, the smart medical room optimization program may be able to determine the location of the clinician to the patient (e.g., whether the clinician has stepped away from the patient, or if the clinician is right next to the patient).

According to at least one embodiment, the smart medical room optimization program may include a smart prescription pad clipboard that provides the status of being pulled out of a physician's white coat and being utilized for writing a prescription.

According to at least one embodiment, the smart medical room optimization program may utilize one or more audio recording devices to capture the conversation in the room. The captured conversation may then be fed into the smart medical room optimization program that also has access to the status of equipment in the smart medical room.

According to at least one embodiment, the smart medical room optimization program may receive signals from the dynamic status of the elements in the smart medical room as the clinician proceeds through the medical encounter. The signals may be utilized to select the correct domain model that best matches the current conversation in the smart medical room. For example, if a nurse enters the room and utilizes the blood pressure cuff and scale, then the domain model for assessing vital signs of a patient is the best domain model to use. In another example, if a physician first enters the room and the patient is sitting upright in the exam chair, there is an initial social greeting conversation that is used in a standard way by the physician to connect with the patient, and thus, the appropriate domain model for social greeting conversations may be utilized.

According to at least one embodiment, the smart medical room optimization program may continue for an entire clinical encounter, and may continuously focus the speech domain model based on observation of the smart medical room and the dynamic device and equipment status in that room. Therefore, the smart medical room optimization program may allow the Speech to Text system to recalibrate to the right domain model without even having to use speech recognition to determine the appropriate domain model.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and a smart medical room optimization program 110a. The networked computer environment 100 may also include a server 112 that is enabled to run a smart medical room optimization program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 3, server computer 112 may include internal components 902a and external components 904a, respectively, and client computer 102 may include internal components 902b and external components 904b, respectively. Server computer 112 may also operate in a cloud computing service model, such as Software as a Service (SaaS), Analytics as a Service (AaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the smart medical room optimization program 110a, 110b may interact with a database 114 that may be embedded in various storage devices, such as, but not limited to a computer/mobile device 102, a networked server 112, or a cloud storage service.

According to the present embodiment, a user using a client computer 102 or a server computer 112 may use the smart medical room optimization program 110a, 110b (respectively) to optimize a smart medical room. The smart medical room optimization method is explained in more detail below with respect to FIG. 2.

Figure 2:
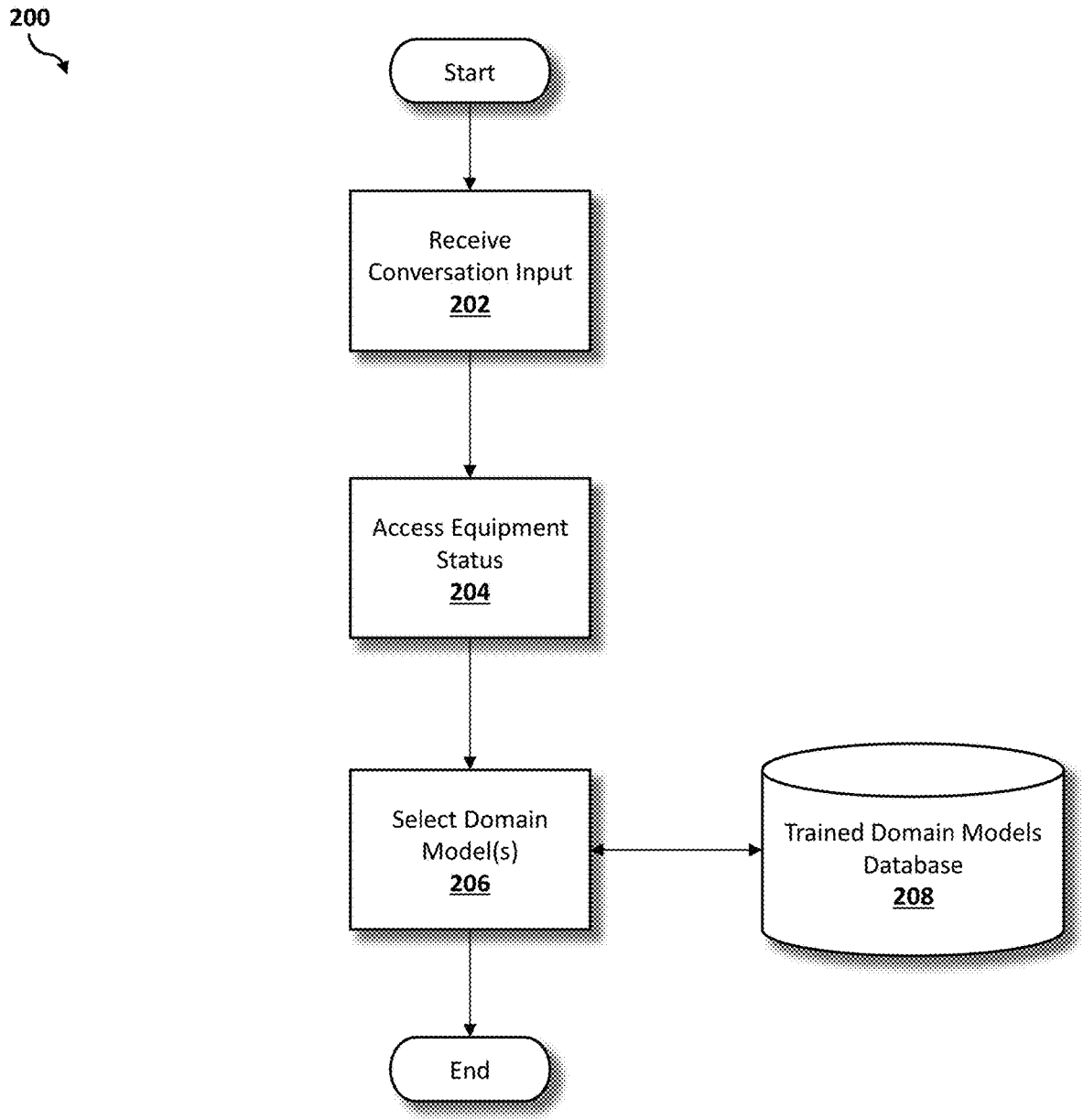
FIG. 2 is an operational flowchart illustrating a process for optimizing speech recognition in a smart medical room according to at least one embodiment.

Referring now to FIG. 2, an operational flowchart illustrating the exemplary smart medical room optimization process 200 used by the smart medical room optimization program 110a, 110b according to at least one embodiment is depicted.

At 202, a conversation is received as input. Using a software program 108 on the user device (e.g., user's computer 102), the smart medical room optimization program 110a, 110b may receive speech patterns (i.e., conversations or piece of verbal data) occurring in a smart medical room between at least one clinician and a patient as input via communication network 116. The smart medical room optimization program 110a, 110b may utilize one or more audio recording devices located at or near the smart medical room to continuously monitor the conversation occurring within the smart medical room or within close proximity to the smart medical room (e.g., with a certain number of feet from the smart medical room). Once the smart medical room optimization program 110a, 110b detects that at least one clinician and the patient located in the smart medical room are present, then the smart medical room optimization program 110a, 110b may be activated, and the received conversation may then be fed into the smart medical room optimization program 110a, 110b by the one or more audio recording devices.

In the present embodiment, the smart medical room optimization program 110a, 110b may be utilized by a clinician (e.g., nurses, medical professional, physician, intern, medical assistant) as a user and by a patient during a medical encounter.

In the present embodiment, even though one or more audio recording devices may be continuously monitoring the speech patterns in the smart medical room, the speech patterns may be received by the smart medical room optimization program 110a, 110b when a clinician and a patient are engaged in a medical encounter.

In at least one embodiment, the smart medical room optimization program 110a, 110b may utilize one or more cameras, active badge technology (i.e., a clinician who enters the smart medical room may have to swipe a badge to identify the clinician), or one or more biometric sensors to detect when at least one clinician is present in the smart medical room.

In at least one embodiment, the smart medical room optimization program 110a, 110b may utilize one or more cameras, or one or more biometric devices associated with biometric sensors to determine the proximity of the one or more clinicians to the patient in the smart medical room.

In at least one embodiment, the smart medical room optimization program 110a, 110b may utilize one or more biometric sensors (e.g., at least one device to detect an increase or decrease in body heat, at least one device to determine a change in weight, at least one device to determine a temperature change) associated with one or more medical equipment (e.g., bed, chairs, wheelchairs) and one or more cameras to confirm the presence of the patient in the smart medical room. In at least one embodiment, the smart medical room optimization program 110a, 110b may utilize one or more biometric sensors (e.g., at least one finger print recognition device, at least one facial recognition device, at least one voice pattern recognition device, at least one iris recognition device, at least one retinal recognition device, at least one hand geometry recognition device, at least one palm print recognition device, at least one walking gait recognition device) to confirm the identity of the patient in the smart medical room. For example, the smart medical room optimization program 110a, 110b may utilize a voice pattern recognition device to determine that patient, with limited mobility and significant physical injuries, is present. The smart medical room optimization program 110a, 110b may, in another example, utilize a facial recognition device for patient to perform a scan when the patient exits or enters the smart medical room, when the patient has frequent visitors in the smart medical room.

In the present embodiment, a medical professional may identify the particular biometric sensors to be utilized in the smart medical room to determine whether a clinician or a patient is present in the smart medical room. The medical professional may consider the severity of the patient's condition, the estimated number of clinicians that may be examining or evaluating the patient, the length of the patient's stay (e.g., hospitalization), the expected frequency of visitors, and the presence of any pre-existing conditions or restrictions that may limit the usability of certain biometric devices (e.g., for a patient with a hearing impairment, a voice pattern recognition device may not be useful to determine the presence of the patient). In at least one embodiment, with the assistance of a medical professional, the patient may select the type of biometric devices utilized in the smart medical room to detect the presence of the patient and to confirm the identity of the patient.

In the present embodiment, for a new patient or a return patient who never provided the necessary physiological information for the biometric sensors associated with the smart medical room optimization program 110a, 110b, the patient may provide the necessary physiological information (e.g., voice samples, finger prints, scans of the face, retina, iris, palm or hand, walking gait sample) for the biometric sensors associated with the smart medical room during the registration or admission to the medical facility. In at least one embodiment, if the patient is a return patient and previously provided the necessary physiological information for the biometric sensors, then, unless there is a change to the physiological information (e.g., change in voice patterns, walking gait), the patient may not have to provide the necessary physiological information for the smart medical room optimization program 110a, 110b.

For example, a cardiologist enters the smart medical room of Patient A, while Patient A is sitting upright in a medical chair. Upon entering the smart medical room, the cardiologist swipes the cardiologist's hospital badge which identifies the cardiologist and records the time that the cardiologist entered smart medical room. The cardiologist then begins to ask Patient A about how Patient A feels today. The smart medical room optimization program 110a, 110b receives input from the audio recording devices in the smart medical room that a conversation has begun between the cardiologist and Patient A.

In another embodiment, in the event that the patient is incapacitated or previously appoints another person to make medical decisions on behalf of the patient, the smart medical room optimization program 110a, 110b may include the necessary physiological information of close family members (e.g., spouse, adult children, parent) or friends (i.e., patient agent) who may engage in a medical encounter with a clinician on behalf of the patient. The smart medical room optimization program 110a, 110b may be activated when at least one clinician is present and the necessary physiological information associated with the patient agent is detected, even if the necessary physiological information of the patient is absent. The necessary physiological information associated with the patient agent may be provided before, during or after the registration or admission process for the patient.

Next, at 204, the equipment status is accessed. Using a software program 108 on the user device (e.g., user's computer 102), the smart medical room optimization program 110a, 110b may access the status of medical equipment located in a smart medical room via communication network 116. Once the smart medical room optimization program 110a, 110b is activated and a conversation is received as input by the one or more audio recording devices, the smart medical room optimization program 110a, 110b may access the dynamic devices and medical equipment associated with the patient and located in the smart medical room (e.g., examination chair, stethoscope, blood pressure cuff, weight scale, otoscope, syringe, drug infusion device, ophthalmology equipment, medical imaging equipment, smart prescription pad, examination bed). The dynamic devices and medical equipment may be able to provide feedback to the smart medical room optimization program 110a, 110b in regard to their use. For example, even though the smart medical room optimization program 110a, 110b may have access to the drug infusion device, the drug infusion device may not provide a status to the smart medical room optimization program 110a, 110b until the drug infusion device is utilized by at least one clinician during the medical encounter. As such, the smart medical room optimization program 110a, 110b has access to the dynamic devices and medical equipment located in the smart medical room; however, the smart medical room optimization program 110a, 110b may only receive feedback from the dynamic devices and medical equipment utilized during the medical encounter.

In the present embodiment, the dynamic devices and medical equipment may be continuously monitoring the status of the patient (e.g., a tocodynamometer that monitors and records uterine contractions during labor, or a heart rate monitor). However, until a medical encounter is detected, the dynamic device and medical equipment status may not be fed into the smart medical room optimization program 110a, 110b.

Continuing the previous example, during the medical encounter between the cardiologist and Patient A, the cardiologist utilizes the blood pressure cuff to take Patient A's blood pressure. The smart medical room optimization program 110a, 110b detects that, during the medical encounter, the cardiologist began to utilize the blood pressure cuff.

In another embodiment, the smart medical room optimization program 110a, 110b may display the feedback received by the dynamic devices and medical equipment on a screen associated with the user device for the clinician to review independently, or with the patient, before, during or after the medical encounter.

In another embodiment, the feedback provided by the dynamic devices and medical equipment may include a history of the patient status since the last medical encounter with a specific clinician or the patient's last medical encounter with a previous clinician.

Then, at 206, one or more domain models are selected from the trained domain models database 208. Using inputs from at least one camera or proximity sensors associated with a particular dynamic device and medical equipment, the smart medical room optimization program 110a, 110b may detect the use of a particular dynamic device and medical equipment, thereby triggering the switch of the domain model. To optimize the accuracy of the medical information transcribed and generated during the medical encounter, the smart medical room optimization program 110a, 110b may intelligently find the appropriate domain model (i.e., speech domain model or language domain model) based on the received conversation during the medical encounter, the dynamic devices and medical equipment utilized during the medical encounter, and the feedback provided by the dynamic devices and medical equipment during the same medical encounter. For example, the trained domain models database 208 includes a domain model that is trained on the conversations that happen when the clinician is utilizing a stethoscope. As such, when the physician starts to use the stethoscope on the patient, the smart medical room optimization program 110a, 110b may detect that the stethoscope is in use and may trigger the use of a domain model trained on the use of a stethoscope as opposed to another type of domain model. If, at a later point in the medical encounter, the smart medical room optimization program 110a, 110b detects that the smart prescription pad clipboard is engaged to write a prescription, then the smart medical room optimization program 110a, 110b will switch to a different domain model which is trained on conversations between a physician and a patient, when the physician is writing a prescription and discussing the medication with a patient, including adherence and side effects.

In at least one other embodiment, the smart medical room optimization program 110a, 110b may detect the use of certain key words (e.g., "hello," "pain") and phrases (e.g., "how are you doing today", "how is your pain today") that may cause the smart medical room optimization program 110a, 110b to switch the domain model to another domain model involving particular key word(s) or phrase(s).

In at least one other embodiment, the smart medical room optimization program 110a, 110b may detect a change in proximity between the patient and the clinician by utilizing cameras and other signals and biometric sensors located in or near the smart medical room and on the dynamic devices and medical equipment to trigger a switch in the domain model. For example, when the physician raises the exam chair back to the upright position and the physician moves away from the patient located in the exam chair signifying the physical exam is complete and the physician starts another phase of the exam to assess the patient's condition, the smart medical room optimization program 110a, 110b is triggered that the domain model should be changed to a domain model trained on patient assessment.

Additionally, as the focus changes during the medical encounter (e.g., the use of a particular key word or phrase, or a change in the proximity between the clinician and the patient), the smart medical room optimization program 110a, 110b may automatically select another appropriate domain model from the trained domain models database 208 for another portion of the medical encounter. The smart medical room optimization program 110a, 110b may then utilize another software program 108 to switch to the newly selected domain model from the trained domain models database 208. The conversation received by one or more audio recording devices, and the feedback provided by the dynamic devices and medical equipment during the medical encounter may be utilized by the smart medical room optimization program 110a, 110b to determine whether another domain model may be necessary.

In the present embodiment, the smart medical room optimization program 110a, 110b may utilize another software program 108 to train the domain models stored in the trained domain models database 208. The software program 108 utilized to train the domain models may receive feedback from the users of the smart medical room optimization program 110a, 110b. Such feedback may be utilized to improve how domain models are trained and improve the accuracy of the trained domain models utilized by the smart medical room optimization program 110a, 110b.

Once the correct domain model is selected, the smart medical room optimization program 110a, 110b may utilize an external Speech to Text system (e.g., Speech to Text system by IBM®) to transcribe the conversations during the medical encounter into a written transcript for use by the clinician and the patient (if necessary). The smart medical room optimization program 110a, 110b may leverage the capability of dynamically selecting the domain models as enabling art, and the external Speech to Text system may permit the smart medical room optimization program 110a, 110b to select an appropriate domain model. The smart medical room optimization program 110a, 110b may further utilize the external Speech to Text system to process the audio recordings generated during the medical encounter, until the smart medical room optimization program 110a, 110b detects the use of a different dynamic device and medical equipment or use of a particular key word or phrase and then the domain model may be switched. During the course of the medical encounter, the signals received by the sensors on the dynamic devices and medical equipment and in or near the smart medical room may cause the domain models to switch or change on multiple occasions.

Additionally, although the external Speech to Text system may possess the ability to select different domain models, the smart medical room optimization program 110a, 110b may utilize the knowledge of the dynamic device and medical equipment status in a smart medical room as input in focusing the domain model and improving accuracy over the course of a medical encounter or examination.

In at least one embodiment, the smart medical room optimization program 110a, 110b may generate a message (i.e., a visual message, such as a green light turned on in the smart medical room, or audible message or sound) to the clinician advising the clinician that a domain model is currently in use. During the training/validation phase, the smart medical room optimization program 110a, 110b may provide an optional notification to the clinician on what domain model is in use for the clinician to provide feedback to the smart medical room optimization program 110a, 110b, and for the clinician to confirm or correct the domain model selected. The feedback may include how the smart medical room optimization program 110a, 110b is working, and any recommended changes. Since the clinicians may prefer no distractions during the medical encounter, the optional notification may be deactivated after the training/validation phase is completed.

Continuing the previous example, when the cardiologist and Patient A started the medical encounter with simple greetings, the smart medical room optimization program 110a, 110b selected a domain model, from the trained domain model database 208, that is trained on simple greetings during a medical encounter, and when the smart medical room optimization program 110a, 110b detected that the cardiologist was utilizing the blood pressure cuff, then the smart medical room optimization program 110a, 110b was triggered to switch the domain model to another domain model that is trained on the use of blood pressure cuffs.

The functionality of a computer may be improved by the smart medical room optimization program 110a, 110b because the smart medical room optimization program 110a, 110b may utilize biometric sensors and signals associated with dynamic devices and medical equipment in a smart medical room to intelligently select a domain model from a trained domain model database 208 to utilize during a medical encounter. The selected domain model may be utilized to optimize the accuracy of the medical information transcribed and generated during the medical encounter.

It may be appreciated that FIG. 2 provides only an illustration of one embodiment and does not imply any limitations with regard to how different embodiments may be implemented. Many modifications to the depicted embodiment(s) may be made based on design and implementation requirements.

Figure 3:
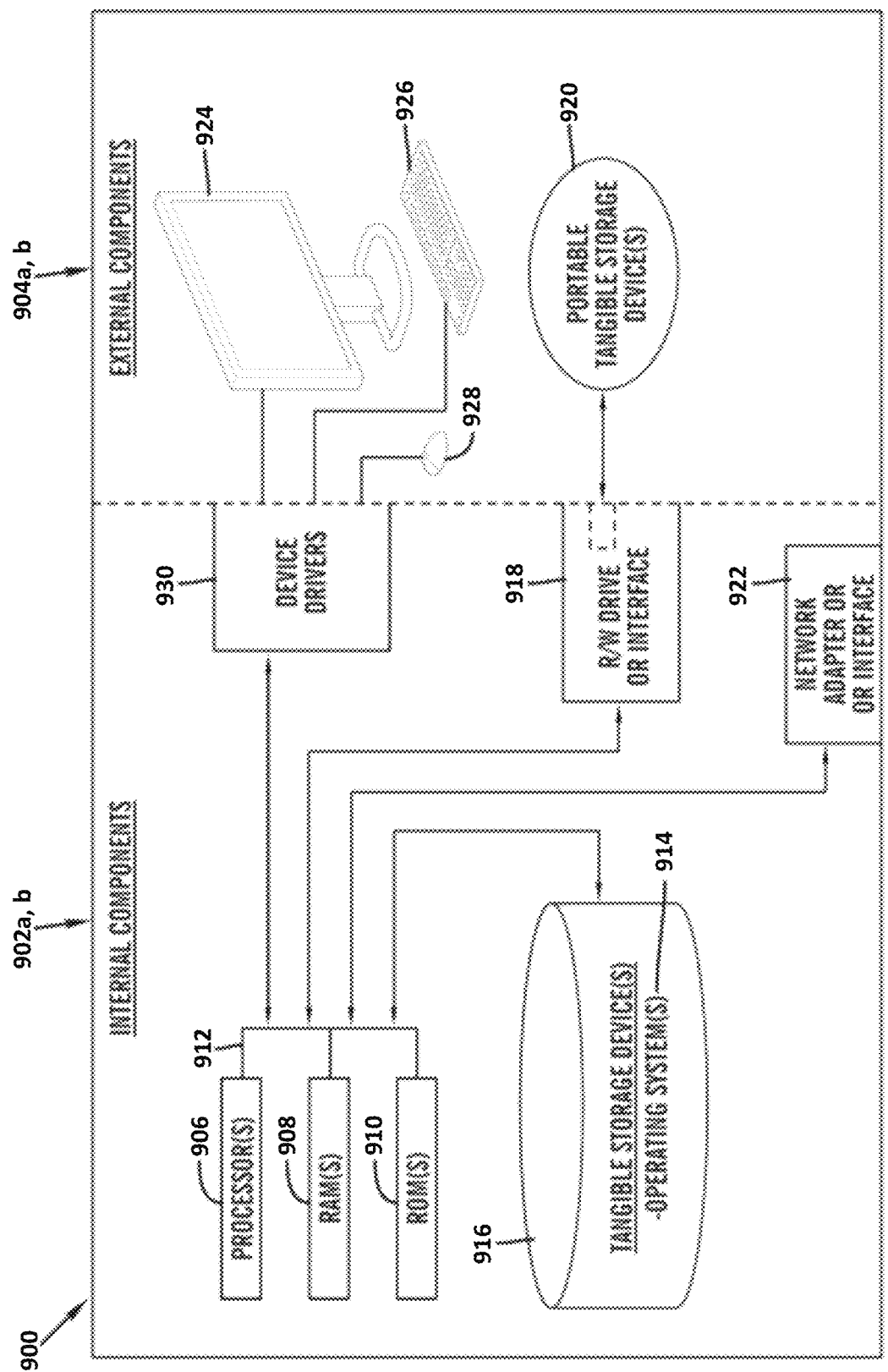
FIG. 3 is a block diagram of internal and external components of computers and servers depicted in FIG. 1 according to at least one embodiment.

FIG. 3 is a block diagram 900 of internal and external components of computers depicted in FIG. 1 in accordance with an illustrative embodiment of the present invention. It should be appreciated that FIG. 3 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902 a, b and external components 904 a, b illustrated in FIG. 3. Each of the sets of internal components 902 a, b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108 and the smart medical room optimization program 110a in client computer 102, and the smart medical room optimization program 110b in network server 112, may be stored on one or more computer-readable tangible storage devices 916 for execution by one or more processors 906 via one or more RAMs 908 (which typically include cache memory). In the embodiment illustrated in FIG. 3, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902 a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the smart medical room optimization program 110a, 110b can be stored on one or more of the respective portable computer-readable tangible storage devices 920, read via the respective R/W drive or interface 918 and loaded into the respective hard drive 916.

Each set of internal components 902 a, b may also include network adapters (or switch port cards) or interfaces 922 such as a TCP/IP adapter cards, wireless Wi-Fi interface cards, or 3G or 4G wireless interface cards or other wired or wireless communication links. The software program 108 and the smart medical room optimization program 110a in client computer 102 and the smart medical room optimization program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the smart medical room optimization program 110a in client computer 102 and the smart medical room optimization program 110b in network server computer 112 are loaded into the respective hard drive 916. The network may comprise copper wires, optical fibers, wireless transmission, routers, firewalls, switches, gateway computers and/or edge servers.

Each of the sets of external components 904 a, b can include a computer display monitor 924, a keyboard 926, and a computer mouse 928. External components 904 a, b can also include touch screens, virtual keyboards, touch pads, pointing devices, and other human interface devices. Each of the sets of internal components 902 a, b also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Analytics as a Service (AaaS): the capability provided to the consumer is to use web-based or cloud-based networks (i.e., infrastructure) to access an analytics platform. Analytics platforms may include access to analytics software resources or may include access to relevant databases, corpora, servers, operating systems or storage. The consumer does not manage or control the underlying web-based or cloud-based infrastructure including databases, corpora, servers, operating systems or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
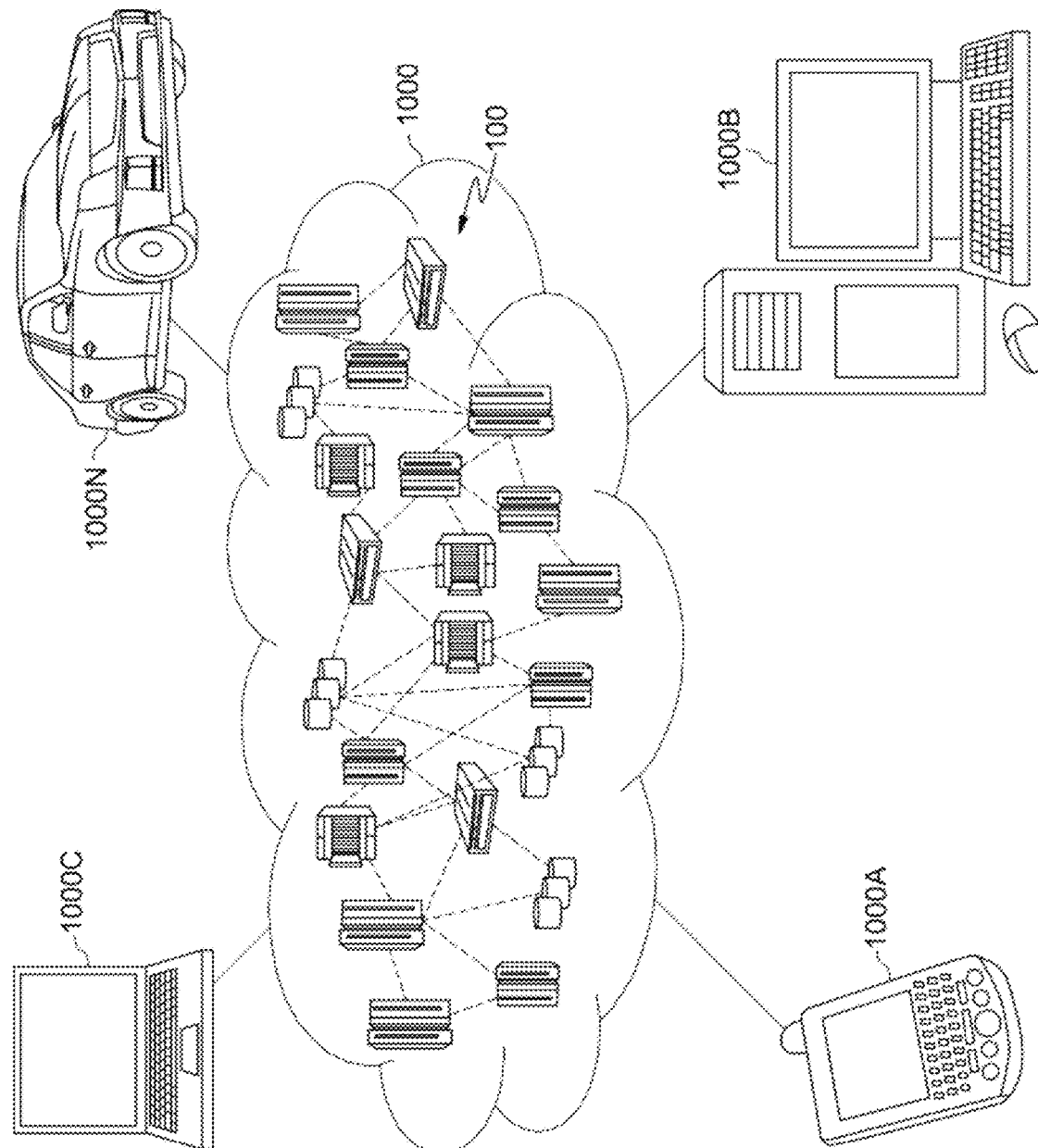
FIG. 4 is a block diagram of an illustrative cloud computing environment including the computer system depicted in FIG. 1, in accordance with an embodiment of the present disclosure.

Referring now to FIG. 4, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 4 are intended to be illustrative only and that computing nodes 100 and cloud computing environment 1000 can communicate with any type of computerized device over any type of network and/or network addressable connection (e.g., using a web browser).

Figure 5:
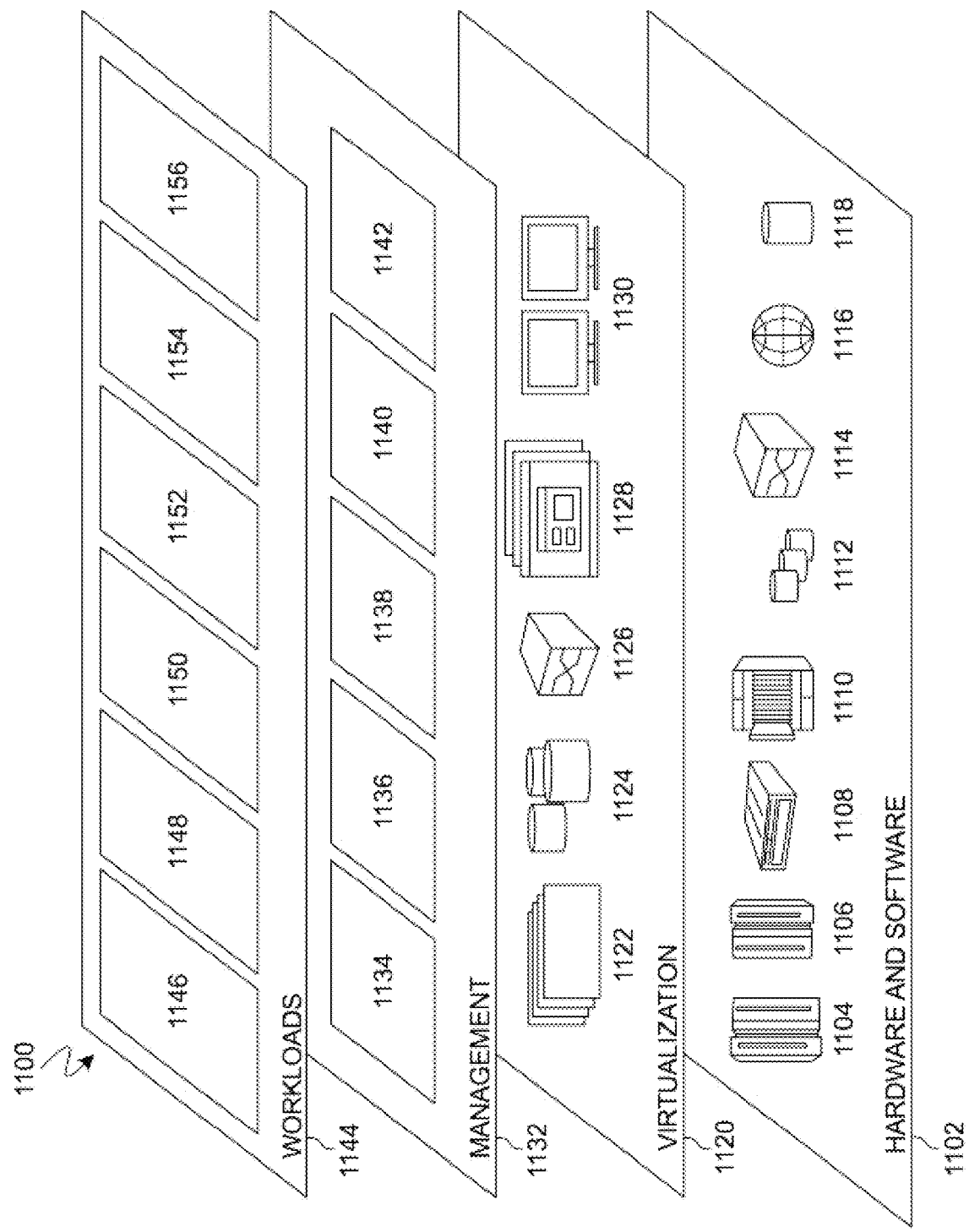
FIG. 5 is a block diagram of functional layers of the illustrative cloud computing environment of FIG. 4, in accordance with an embodiment of the present disclosure.

Referring now to FIG. 5, a set of functional abstraction layers 1100 provided by cloud computing environment 1000 is shown. It should be understood in advance that the components, layers, and functions shown in FIG. 5 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and smart medical room optimization 1156. A smart medical room optimization program 110a, 110b provides a way to optimize a smart medical room for speech recognition systems.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for optimizing speech recognition in a smart medical room, the method comprising:
  receiving a piece of verbal data associated with a medical encounter from one or more audio recording devices;
  accessing a plurality of signals from a plurality of biometric sensors associated with a plurality of medical equipment associated with the smart medical room based on the received piece of verbal data associated with the medical encounter; and
  selecting, from a database, one or more speech domain models based on the accessed plurality of signals from the plurality of biometric sensors associated with the plurality of medical equipment,
    wherein the one or more speech domain models are utilized to optimize a transcription of speech during the medical encounter in the smart medical room,
    wherein the one or more speech domain models are trained with one or more feedback from the clinician based on the medical encounter and from a continuous feedback display in the smart medical room,
    wherein the one or more feedback from the clinician is based on an optional notification to the clinician to confirm the one or more speech models in use.

2. The method of claim 1 in which the medical encounter includes at least one clinician and a patient.

3. The method of claim 2, further comprising:
  identifying the at least one clinician is located in the smart medical room by utilizing an active badge device and one or more cameras; and
  detecting a proximity of the identified at least one clinician to the patient by utilizing the one or more cameras.

4. The method of claim 2, further comprising:
  determining that the patient is present in the smart medical room by utilizing one or more cameras and one or more biometric devices; and
  confirming the identity of the patient in the smart medical room by utilizing one or more cameras and one or more biometric devices.

5. The method of claim 4 in which the one or more biometric devices utilized to confirm the identity of the patient in the smart medical room is selected from the group consisting of:
  (i) a finger print recognition device,
  (ii) a facial recognition device,
  (iii) a voice pattern recognition device,
  (iv) an iris recognition device,
  (v) a retinal recognition device,
  (vi) a hand geometry recognition device,
  (vii) a palm print recognition device, and
  (viii) a walking gait recognition device.

6. The method of claim 1 in which the plurality of medical equipment is selected from the group consisting of:
  (i) a smart prescription clipboard,
  (ii) an examination bed,
  (iii) an examination chair,
  (iv) a stethoscope,
  (v) a blood pressure cuff,
  (vi) a weight scale,
  (vii) an otoscope,
  (viii) a syringe, (ix) a drug infusion device,
(x) an ophthalmology device, and
(xi) a medical imaging device.

7. The method of claim 1, wherein selecting, from the database, the one or more speech domain models based on the accessed plurality of signals from the plurality of biometric sensors associated with the plurality of medical equipment, further comprises:
   detecting a change in the use of at least one medical device associated with the plurality of medical equipment; and
   triggering a switch of a current speech domain model utilized during the medical encounter.

8. The method of claim 1, further comprising:
   determining the received piece of verbal data is selected from the group consisting of:
      (i) a key word, and
      (ii) a phrase; and
   triggering a switch of a current speech domain model utilized during the medical encounter.

9. A computer system for optimizing speech recognition in a smart medical room, comprising:
   one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:
   receiving a piece of verbal data associated with a medical encounter from one or more audio recording devices;
   accessing a plurality of signals from a plurality of biometric sensors associated with a plurality of medical equipment associated with the smart medical room based on the received piece of verbal data associated with the medical encounter; and
   selecting, from a database, one or more speech domain models based on the accessed plurality of signals from the plurality of biometric sensors associated with the plurality of medical equipment,
      wherein the one or more speech domain models are utilized to optimize a transcription of speech during the medical encounter in the smart medical room,
      wherein the one or more speech domain models are trained with one or more feedback from the clinician based on the medical encounter and from a continuous feedback display in the smart medical room,
      wherein the one or more feedback from the clinician is based on an optional notification to the clinician to confirm the one or more speech models in use.

10. The computer system of claim 9 in which the medical encounter includes at least one clinician and a patient.

11. The computer system of claim 10, further comprising:
   identifying the at least one clinician is located in the smart medical room by utilizing an active badge device and one or more cameras; and
   detecting a proximity of the identified at least one clinician to the patient by utilizing the one or more cameras.

12. The computer system of claim 10, further comprising:
   determining that the patient is present in the smart medical room by utilizing one or more cameras and one or more biometric devices; and
   confirming the identity of the patient in the smart medical room by utilizing one or more cameras and one or more biometric devices.

13. The computer system of claim 12 in which the one or more biometric devices utilized to confirm the identity of the patient in the smart medical room is selected from the group consisting of:
   (i) a finger print recognition device,
   (ii) a facial recognition device,
   (iii) a voice pattern recognition device,
   (iv) an iris recognition device,
   (v) a retinal recognition device,
   (vi) a hand geometry recognition device,
   (vii) a palm print recognition device, and
   (viii) a walking gait recognition device.

14. The computer system of claim 9 in which the plurality of medical equipment is selected from the group consisting of:
   (i) a smart prescription clipboard,
   (ii) an examination bed,
   (iii) an examination chair,
   (iv) a stethoscope,
   (v) a blood pressure cuff,
   (vi) a weight scale,
   (vii) an otoscope,
   (viii) a syringe,
   (ix) a drug infusion device,
   (x) an ophthalmology device, and
   (xi) a medical imaging device.

15. The computer system of claim 9, wherein selecting, from the database, the one or more speech domain models based on the accessed plurality of signals from the plurality of biometric sensors associated with the plurality of medical equipment, further comprises:
   detecting a change in the use of at least one medical device associated with the plurality of medical equipment; and
   triggering a switch of a current speech domain model utilized during the medical encounter.

16. The computer system of claim 9, further comprising:
   determining the received piece of verbal data is selected from the group consisting of:
      (i) a key word, and
      (ii) a phrase; and
   triggering a switch of a current speech domain model utilized during the medical encounter.

17. A computer program product for optimizing speech recognition in a smart medical room, comprising:
   one or more non-transitory computer-readable storage media and program instructions stored on at least one of the one or more tangible storage media, the program instructions executable by a processor to cause the processor to perform a method comprising:
   receiving a piece of verbal data associated with a medical encounter from one or more audio recording devices;
   accessing a plurality of signals from a plurality of biometric sensors associated with a plurality of medical equipment associated with the smart medical room based on the received piece of verbal data associated with the medical encounter; and
   selecting, from a database, one or more speech domain models based on the accessed plurality of signals from the plurality of biometric sensors associated with the plurality of medical equipment,
      wherein the one or more speech domain models are utilized to optimize a transcription of speech during the medical encounter in the smart medical room,
      wherein the one or more speech domain models are trained with one or more feedback from the clinician based on the medical encounter and from a continuous feedback display in the smart medical room,
wherein the one or more feedback from the clinician is based on an optional notification to the clinician to confirm the one or more speech models in use.

18. The computer program product of claim 17 in which the medical encounter includes at least one clinician and a patient.

19. The computer program product of claim 18, further comprising:
   identifying the at least one clinician is located in the smart medical room by utilizing an active badge device and one or more cameras; and
   detecting a proximity of the identified at least one clinician to the patient by utilizing the one or more cameras.

20. The computer program product of claim 18, further comprising:
   determining that the patient is present in the smart medical room by utilizing one or more cameras and one or more biometric devices; and
   confirming the identity of the patient in the smart medical room by utilizing one or more cameras and one or more biometric devices.

* * * * *